United States Patent
Lambert

(12) 
(10) Patent No.: US 6,488,028 B1
(45) Date of Patent: Dec. 3, 2002

(54) DEVICE FOR RECOVERING ANAESTHETIC

(75) Inventor: Hans Lambert, Stockholm (SE)

(73) Assignee: Hudson RCI AB (SE)

( * ) Notice: Subject to any disclaimer, the term of this patent is extended or adjusted under 35 U.S.C. 154(b) by 0 days.

(21) Appl. No.: 09/051,092

(22) PCT Filed: Oct. 10, 1996

(86) PCT No.: PCT/SE96/01291

§ 371 (c)(1), (2), (4) Date: Apr. 14, 1998

(87) PCT Pub. No.: WO97/14465

PCT Pub. Date: Apr. 24, 1997

(30) Foreign Application Priority Data

Oct. 16, 1995 (SE) ................................................ 9503614

(51) Int. Cl.[7] .................................................. A62B 7/10
(52) U.S. Cl. .............................. 128/205.12; 128/204.13
(58) Field of Search ...................... 128/202.22, 203.14, 128/204.13, 204.14, 204.15, 204.16, 205.12

(56) References Cited

U.S. PATENT DOCUMENTS

| | | | | |
|---|---|---|---|---|
| 658,793 A | * | 10/1900 | Lockey ................... | 128/204.13 |
| 3,351,057 A | * | 11/1967 | Goodyear et al. ..... | 128/202.22 |
| 3,489,144 A | * | 1/1970 | Dibelius et al. ........ | 128/205.12 |
| 3,573,158 A | * | 3/1971 | Pall et al. ................ | 162/131 |
| 3,782,083 A | * | 1/1974 | Rosenberg ............. | 128/205.12 |
| 5,044,361 A | * | 9/1991 | Werner et al. ......... | 128/204.16 |
| 5,143,060 A | * | 9/1992 | Smith ..................... | 128/205.12 |
| 5,213,096 A | * | 5/1993 | Kihlberg et al. ....... | 128/205.12 |
| 5,231,980 A | * | 8/1993 | Filipovic et al. ....... | 128/205.12 |
| 5,471,979 A | * | 12/1995 | Psaros et al. .......... | 128/203.12 |
| 5,592,934 A | * | 1/1997 | Thwaites ............... | 128/203.14 |
| 6,116,235 A | * | 9/2000 | Walters et al. ......... | 128/205.12 |
| 6,152,133 A | * | 11/2000 | Psaros et al. .......... | 128/205.12 |

FOREIGN PATENT DOCUMENTS

| | | |
|---|---|---|
| GB | 2255912 | 11/1992 |
| SE | 459155 | 6/1989 |
| SE | 467996 | 10/1992 |

\* cited by examiner

*Primary Examiner*—Aaron J. Lewis
(74) *Attorney, Agent, or Firm*—Knobbe, Martens, Olson & Bear LLP

(57) ABSTRACT

A device for recovering anaesthetic. During the administration of inhaled anaesthetic, the device is connected to a patient. It includes an anaesthetic evaporator for supplying anaesthetic to the patient and an absorption filter for absorption and desorption of the medium. The device includes a body placed between the absorption filter and the patient with the gases breathed by the patient passing across the body and the anaesthetic evaporating on the surface thereof. The absorption filter is in the form of a flat element placed in the flow path of a gas breathed by the patient and contains fibers of active carbon. The absorption filter is movably arranged in a housing between a position in which substantially all the gases breathed pass through the filter and the position in which a small portion of the gases breathed passes therethrough.

14 Claims, 2 Drawing Sheets

DEVICE FOR RECOVERING ANAESTHETIC

TECHNICAL FIELD

The present invention relates to a device for recovering anaesthetic during the use of inhaled anaesthetics. The device is connected to a patient and comprises an anaesthetic evaporator for supplying anaesthetic to the patient and an absorption filter for absorption and desorption of the medium.

BACKGROUND ART

DISCUSSION OF THE BACKGROUND

In the evaporator a fresh gas flow is conducted past the anaesthetic, in liquid phase, whereupon the medium evaporates in part of the fresh gas flow. This gas is mixed incompletely or unevenly with the gas breathed by the patient when it enters the tube since it enters through said opening. Since the supply of anaesthetic is also affected both by the flow and pressure of the gas breathed by the patient, it is difficult to know how much anaesthetic is actually being supplied to the patient.

The absorption filter is in the form of a body or container holding active carbon, for instance, in granular or powder form. Large quantities of such material are necessary for the absorption effect to be efficient. This means that the filter must be large and thus requires considerable space as well as increasing the quantity of carbon dioxide that is re-inhaled. The material must also be surrounded by a suitable filter to prevent the granules/powder from flowing into the patient's lungs. The carbon also absorbs a certain amount of gas which therefore fails to benefit the patient. In some cases the breathing resistance may be considerable.

When using the device according to SE-B 459 155 it is impossible to abruptly alter or disconnected the supply of anaesthetic to the patient since some medium remains in the absorption filter. The remaining medium is admittedly gradually aired out but this takes time and in the meanwhile the patient is receiving an undesired supply of anaesthetic.

Neither does the device according to SE-B 459 155 allow the supply of anaesthetic to be closed off should the patient temporarily stop breathing.

DESCRIPTION OF THE INVENTION

One object of the present invention is at least partially to eliminate the summary of the invention provide a device having one or more of the following advantages:

Supply of anaesthetic to the gas breathed by the patient in exact quantities and in such a manner that the consumption of anaesthetic can be accurately controlled.

The absorption filter requires little volume and takes up little space, in spite of breathing resistance being maintained or decreased.

The absorption filter need not be surrounded by an extra filter.

The supply of anaesthetic from the absorption filter to the patient can be quickly cut off.

The supply of anaesthetic from the evaporator to the patient can be closed off if the patient stops breathing temporarily.

This object is fulfilled by the device according to the invention being given the features defined in the characterizing part of the claims.

DISCUSSION OF THE PREFERRED EMBODIMENTS

Figure 1:
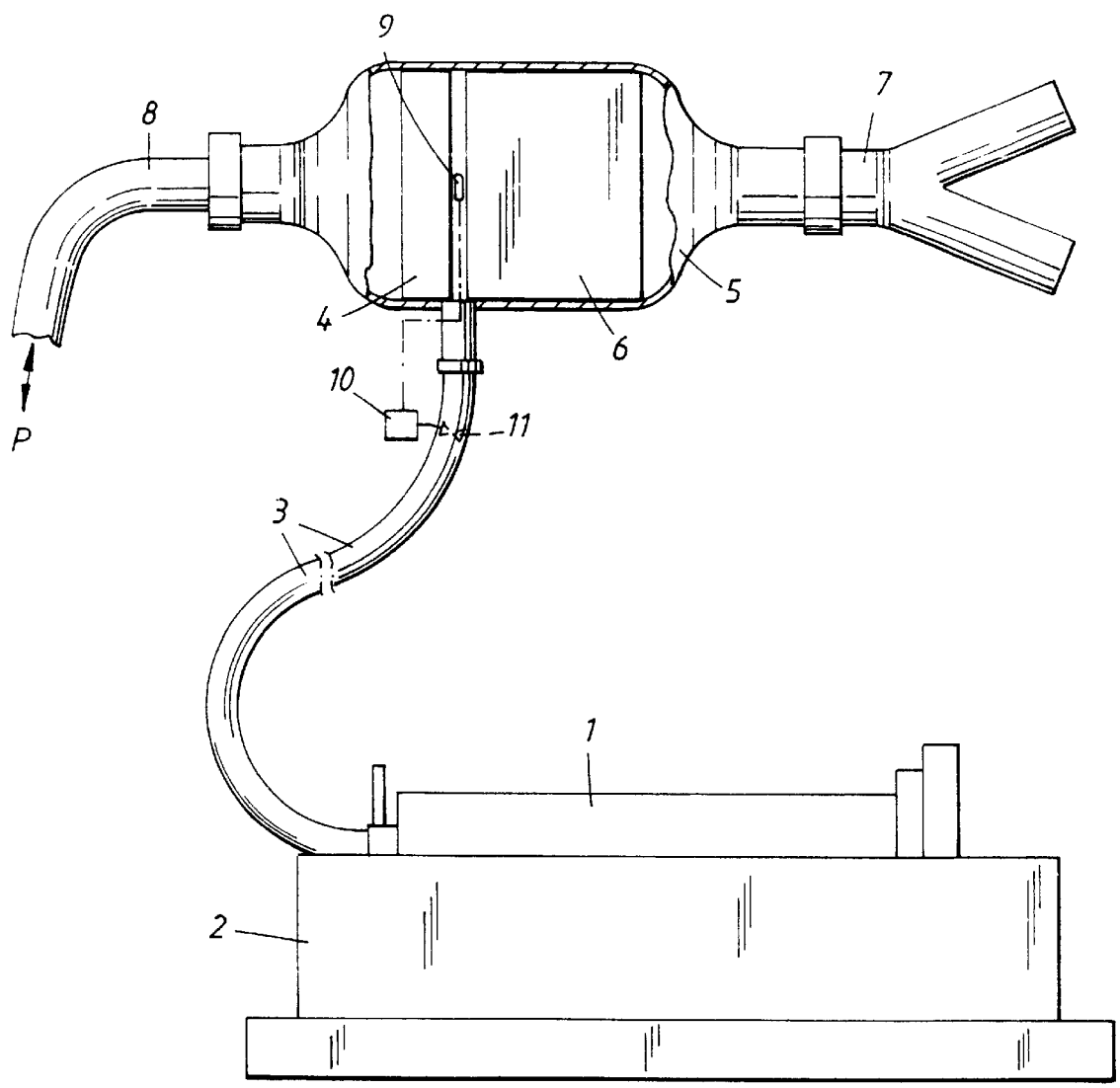
FIG. 1 is a schematic view from the side, partly in section, of one embodiment of the invention according to the present invention.

FIG. 1 shows a container 1 containing anaesthetic with high vapour pressure and in liquid phase. A pump 2 is connected to the container 1 and supplies the liquid to an evaporator 4 via a tube 3 at a velocity that can be varied depending on the need for anaesthetic. The evaporator is applied inside a housing 5 which also contains an absorption-desorption filter 6. The evaporator comprises a body on the surface of which the anaesthetic fluid evaporates. This surface is preferably large in area. The body may be porous, for instance, with the inlet situated centrally in the body or it may be provided with flanges to distribute the anaesthetic uniformly.

One end of the housing 5 is preferably detachably connected to a respirator or the like, not shown, via a tube 7, and the other end of the housing is preferably detachably connected to a patient P via a tube 8. The gases breathed flow between the respirator and the patient in the direction of the arrows, also passing the evaporator 4 and the absorption filter 6. When the patient inhales, a predetermined quantity of anaesthetic will be supplied which, upon exhaling, will be partly deposited in the filter 6 and is therefore recovered to be inhaled again.

The absorption material in the filter 6 consists of active carbon in the form of fibres or bound to fibres woven to form fabric or wadding. The volume of the filter 6 is thus small since its efficiency per weight and volume unit is large which in turn means that the quantity of anaesthetic gas enclosed in the filter is small. Since the woven material forms a self-carrying unit, no extra carrier is necessary. The fabric can be shaped so that its breathing resistance is slight and it can be treated with bacteria-filtering means or be laminated with a bacteria filter.

The absorption filter 6 may be shaped as a thin disc, as shown in FIG. 1, thus reducing the extension of the housing in the direction of the gases being breathed, to a minimum. If the housing 5 is made lower, the disc can be made rotatable in this, rotation being effected from the outside of the housing by a knob, for instance (not shown). The disk then functions as a damper which, when active, assumes the position shown in FIG. 1 in which all the gas breathed by the patient that flows through the housing also flows past the damper and, when most inactive, is substantially in horizontal position. In the latter position the flow of anaesthetic from the filter 6 to the patient is minimized when the supply of anaesthetic to the evaporator 4 is cut off.

FIG. 1 also shows a device for closing off the supply of anaesthetic should the patient temporarily stop breathing. The device comprises a flow gauge 9 applied in a housing 5 which senses if the gas breathed is flowing to and/or from the patient. The flow gauge 9 is suitably applied between the evaporator 4 and the filter 6 but may instead be placed somewhere else in the housing 5 or in the tube 7 or 8. The gauge 9 is connected to an electronic or mechanical converter 10 connected to a valve 11 in the tube 3. When the gauge 9 senses the existence of a gas flow the valve 11 is open and allows through anaesthetic, and when the gauge 9 senses that the gas flow has ceased for a certain period, the valve is closed via the converter 10. The gauge 9 may consist, for instance, of two pressure sensors, one on each side of a flow resistor or a thermistor which is cooled by the flow, or a propeller which senses the flow and then influences an optical cell.

Figure 2:
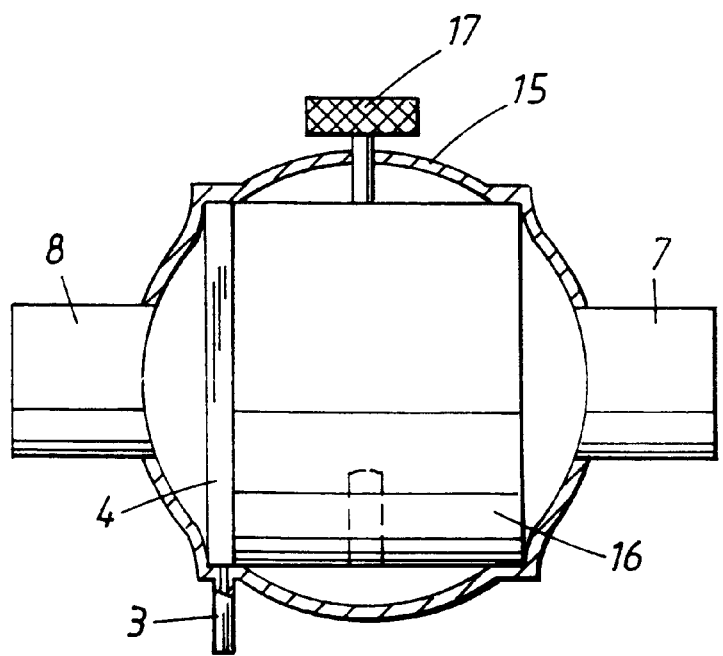
FIGS. 2 and 3 are schematic views from the side, partly in section, of a second embodiment of the device according to the present invention.
Figure 3:
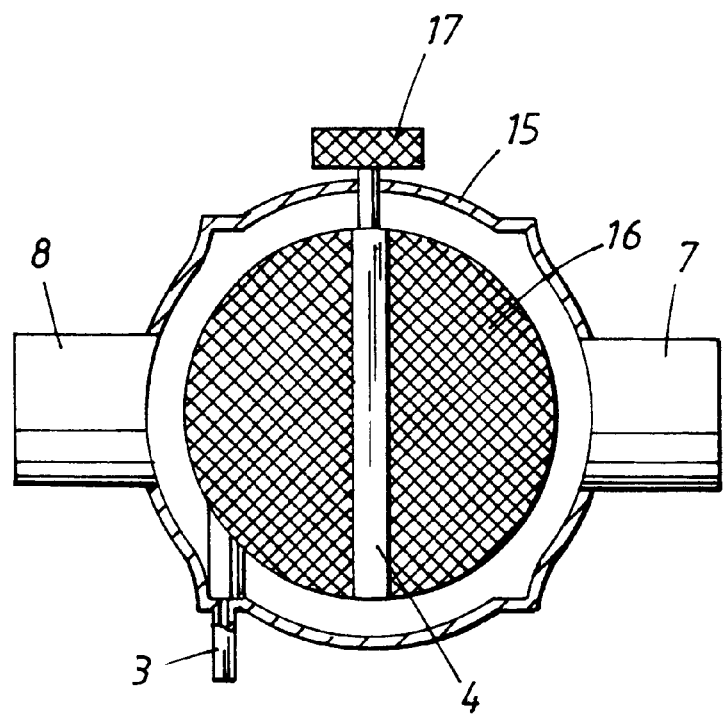

FIG. 2 shows a second embodiment of the casing containing the evaporator and absorption filter. The housing, designated 15, is spherical and the absorption filter, designated 16, is in the form of a circular cylinder having its longitudinal axis parallel with the tubes 7 and 8 and in the position shown in FIG. 2. The circular end edges of the cylinder 16 abut and seal against the inside of the housing 15. A knob 17 on the outside of the housing 15 is connected to the cylinder 16. When the knob 17 is turned 90° the cylinder 16 assumes the position shown in FIG. 3 so that the gases breathed can flow between the envelope surface of the cylinder and the inside of the housing. The cylinder 16 consists of a gas-tight outer casing and contains active carbon in powder or granular form.

Although only a few embodiments of the device according to the invention have been described above and shown in the drawings it should be understood that the invention is not limited to these embodiments, but only by the limitations defined in the appended claims.

What is claimed is:

1. A device for recovering anaesthetic during use of inhaled anesthetics and adapted for connection to a patient breathing circuit comprising a housing having an inlet adapted for connection to a respirator and an outlet adapted for connection to a patient, the interior of said housing forming a bidirectional passageway between the inlet and the outlet, an anaesthetic evaporator for supplying anaesthetic to a patient and an anaesthetic absorption filter for absorbing and desorbing anaesthetic, wherein the evaporator and the absorption filter are arranged in series in the housing between the inlet and the outlet with the evaporator located between the absorption filter and the outlet, and whereby gases breathed by the patient and flowing between the inlet and the outlet pass across both the evaporator and the absorption filter within the housing during inhalation and during exhalation.

2. A device of claim 1, wherein the absorption filter comprises a flat element in the flow path of the gas breathed by the patient and comprises fibers of active carbon.

3. A device of claim 2, wherein the flat element is woven.

4. A device of claim 2 or 3, wherein the flat element comprises or is laminated with a bacteria filter.

5. A device of claim 1 wherein the absorption filter is movably applied in the housing between a position in which substantially all the gases breathed pass through the filter and a position in which a small portion of the gases breathed passes therethrough.

6. A device of claim 5, wherein the absorption filter can be rotated with the aid of a turning element on the outside of the housing.

7. A device of claim 5 or 6, wherein the absorption filter comprises a cylinder and the housing comprises a substantially spherical container, whereby in a first position the cylinder seals against the inside of the container and in a second position it is spaced from the inside of the container.

8. A device of claim 6, wherein the absorption filter comprises a thin, circular disc, whereby in a first position the periphery of the disc seals against the inside of the housing and in a second position the main plane of the disc is substantially parallel with the direction of flow of the gases breathed.

9. A device of claim 1, and a container for holding liquid anaesthetic and tubing connected between the container and the housing for supplying anaesthetic from the container to the housing.

10. A device of claim 9, wherein the evaporator is porous.

11. A device of claim 9, wherein the tubing supplies liquid anaesthetic to the porous evaporator.

12. A device of claim 9, 10 or 11 including a sensor arranged in the housing or in the tubing for sensing the pressure, flow, and/or velocity of the gas flow and for terminating the supply of anaesthetic to the evaporator when the gas flow has ceased for a certain period of time.

13. An apparatus for delivering anaesthetic in a patient breathing circuit comprising:

a housing having an inlet for receiving respiratory gases and an outlet for delivering gases to a patient;

an anaesthetic evaporator and an anaesthetic absorption filter arranged in series in said housing, said housing comprising a bidirectional passageway therein for breathed gases between said inlet and said outlet whereby inhaled and exhaled gases pass across both said evaporator and said absorber during inhalation and during exhalation.

14. A device of claim 13 wherein the absorption filter is movably applied in the housing between a first position in which substantially all the gases breathed pass through the filter and a second position in which a small portion of the gases breathed passes therethrough.

* * * * *